(12) United States Patent
Harms et al.

(10) Patent No.: US 7,896,918 B2
(45) Date of Patent: Mar. 1, 2011

(54) SPACE HOLDER FOR VERTEBRAE OR INTERVERTEBRAL DISCS

(75) Inventors: Jürgen Harms, Karlsruhe (DE); Lutz Biedermann, VS-Villingen (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 0 days.

(21) Appl. No.: 10/568,262

(22) PCT Filed: Aug. 11, 2004

(86) PCT No.: PCT/EP2004/008998
§ 371 (c)(1),
(2), (4) Date: Jun. 30, 2006

(87) PCT Pub. No.: WO2005/013861
PCT Pub. Date: Feb. 17, 2005

(65) Prior Publication Data
US 2007/0129806 A1      Jun. 7, 2007

(30) Foreign Application Priority Data
Aug. 12, 2003    (DE) .................... 103 37 088

(51) Int. Cl.
*A61F 2/44* (2006.01)
(52) U.S. Cl. .............. 623/17.13; 623/17.15; 623/17.16
(58) Field of Classification Search .............. 606/61, 606/246, 279; 623/17.11–17.16
See application file for complete search history.

(56) References Cited

U.S. PATENT DOCUMENTS

| | | | |
|---|---|---|---|
| 4,820,305 A | 4/1989 | Harms et al. | |
| 4,946,378 A * | 8/1990 | Hirayama et al. | 623/17.16 |
| 5,002,576 A | 3/1991 | Fuhrmann et al. | |
| 5,071,437 A | 12/1991 | Steffee | |
| 5,171,281 A | 12/1992 | Parsons et al. | |
| 5,370,697 A | 12/1994 | Baumgartner | |
| 5,609,637 A | 3/1997 | Biedermann et al. | |
| 5,702,450 A | 12/1997 | Bisserie | |
| 5,782,832 A | 7/1998 | Larsen et al. | |
| 5,972,031 A | 10/1999 | Biedermann et al. | |
| 5,989,290 A * | 11/1999 | Biedermann et al. | 623/17.11 |
| 6,402,785 B1 * | 6/2002 | Zdeblick et al. | 623/17.16 |
| 6,758,862 B2 * | 7/2004 | Berry et al. | 623/17.16 |
| 6,960,232 B2 * | 11/2005 | Lyons et al. | 623/17.16 |
| 7,105,024 B2 * | 9/2006 | Richelsoph | 623/17.13 |
| 2003/0009224 A1 * | 1/2003 | Kuras | 623/17.16 |
| 2003/0074076 A1 | 4/2003 | Ferree et al. | |

(Continued)

FOREIGN PATENT DOCUMENTS

DE    36 37 314 A1    5/1988

(Continued)

*Primary Examiner* — Thomas C Barrett
*Assistant Examiner* — Andrew Yang
(74) *Attorney, Agent, or Firm* — Christie, Parker & Hale, LLP

(57) ABSTRACT

The present invention concerns a space holder, especially for vertebrae or intervertebral discs for implantation into human or animal organisms, having a cylinder-like body (1) and, at the ends of the cylinder-like body, means (2) provided for connecting to adjacent body parts, said cylinder-like body (1) essentially being formed as a solid cylinder from at least one material that is elastically deformable under the conditions of use, such that the space holder is compressible and extensible in the axial direction and, with reference to means (2) provided at the ends for connecting the space holder to adjacent body parts, can bend about a radial axis of rotation (13).

21 Claims, 3 Drawing Sheets

U.S. PATENT DOCUMENTS

Figure 1:
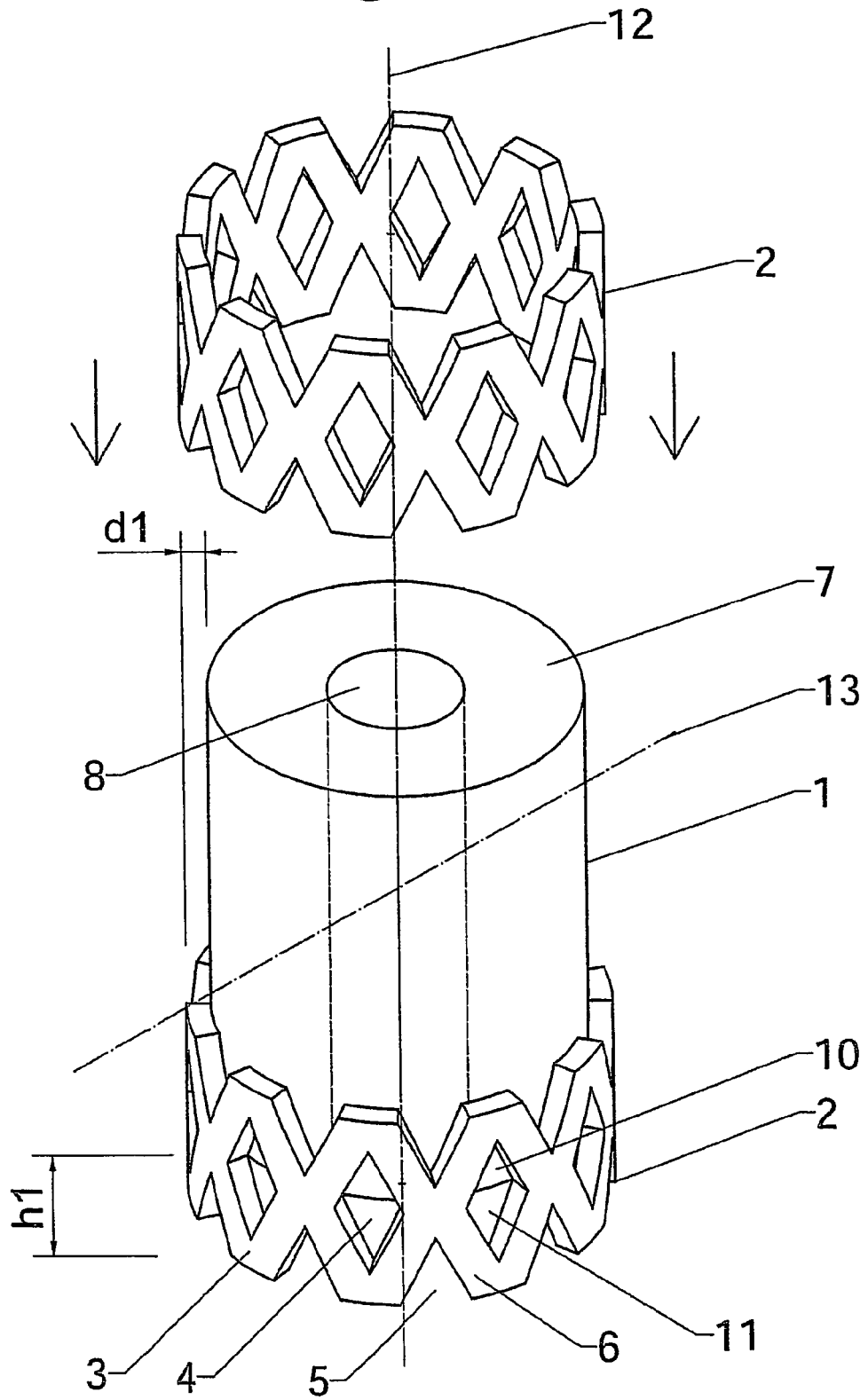

| | | |
|---|---|---|
| 2003/0078667 A1 | 4/2003 | Manasas et al. |
| 2003/0187506 A1 | 10/2003 | Ross et al. |
| 2003/0208272 A1* | 11/2003 | Crozet et al. ............... 623/17.11 |

FOREIGN PATENT DOCUMENTS

| | | |
|---|---|---|
| DE | 43 23 034 C1 | 7/1994 |
| DE | 694 16 588 T2 | 2/1999 |
| DE | 100 56 977 C2 | 4/2003 |
| DE | 698 14 460 T2 | 5/2003 |
| EP | 0 346 129 A1 | 12/1989 |
| EP | 1 041 945 B1 | 5/2003 |
| JP | 03275055 A | 12/1991 |
| WO | WO 02/17825 A2 | 3/2002 |
| WO | WO 02/085261 A1 | 10/2002 |
| WO | WO 03/079939 A1 | 10/2003 |

* cited by examiner

SPACE HOLDER FOR VERTEBRAE OR INTERVERTEBRAL DISCS

CROSS-REFERENCE TO RELATED APPLICATION

This application is a National Phase Patent Application of International Application Number PCT/EP2004/008998 filed Aug. 11, 2004 which claims priority of DE 103 37 088.9 filed Aug. 12, 2003.

The present invention concerns space holders according to the preamble of claim 1.

Space holders, especially for vertebrae and intervertebral discs, which, for example, are used as replacements for a vertebra, have been known for some considerable time in medical technology, as is confirmed by DE 36 37 314 A1 or DE 43 23 034 C1. The space holders used initially (DE 36 37 314A1) have also already undergone numerous further developments, as is shown by U.S. Pat. No. 5,972,031 or DE 43 23 034 C1, to adjust the space holders to the individual needs or to facilitate use, especially for the operator.

Although good results are obtained with the space holders already known, there is at the same time a need to further improve the known space holders, and more especially with regard to more optimum adjustment to the individual requirements of the site of implantation to improve compatibility and usage possibilities for the patient in order to increase their quality of life as well as with regard to improved user-friendliness for the operator who implants the space holder.

An implant is known from DE 100 56 977 C2 that can be used as a replacement for vertebrae or intervertebral discs. These implants have plate-shaped supporting elements between which a pipe-like hollow space is formed by a bellows-like outer wall. Into the hollow space, which is formed by the non-extensible and thus rigid outer wall, the degree of flexibility of which derives only from the bellows-like structure, can be filled bone cement or a flowable or rubber-like elastic compound such that the supporting elements at the ends of the hollow space are given a slight degree of mobility. Although this already provides a certain degree of mobility for a patient fitted with these implants, this solution is unsatisfactory as regards manufacturing effort and functionality. Due to the combination of a rigid outer wall, which is flexible only by mechanical means (bellows-like structure) in conjunction with a soft core, defined setting of the necessary properties as regards mobility is not satisfactorily possible. Moreover, the differential movement between the bellows-like external wall and the flowable or rubber-elastic filling material creates problems at the interface between filling material and outer wall, a fact which also can lead to impairment of the implant's service life.

It is therefore the object of the present invention to create a space holder that is an improvement on the prior art, with said space holder adapting better to the individual requirements of the site of implantation and assuming more diverse functions, especially also with regard to accommodating load, transferring load and mobility. Especially, the purpose of the space holder is to ensure that the patient is burdened as little as possible by the implant and retains or regains as much of their original load-bearing capacity and mobility as possible. Furthermore, the space holder of the invention is intended to simplify the work of the operator and lend itself overall to simple and inexpensive manufacture.

This object is solved by a space holder having the features of patent claim 1. Advantageous embodiments are the subject of the dependent claims.

The basic idea of the invention is that greater variability of the space holder and optimisation of its property profile can be obtained by reshaping the base body usually employed in the form of a lattice-like or cylinder pipe for the space holder such that the functionality is increased and improved. Starting from this idea, the inventor has recognised that this can be achieved in such a way that, according to a first aspect, the rigid and stiff design of the cylinder pipe-like base body is eschewed in favour of an elastic and flexible design of the cylinder-like body and, according to a second aspect, the lattice-like cylinder pipe shape is transformed into a solid shape since, on one hand, the elastic and flexible design of the cylinder-like base body makes it possible for the patient to accommodate mechanical loads more bearably and especially since the mobility, i.e. the mobility of the body parts connected to each other by means of the space holder or the body parts adjacent to the space holder, is improved. Moreover, on the other hand, the solid form of the cylinder-shaped base body facilitates overall better distribution of load and especially a simple, elastic, flexible embodiment with a long service life.

By elastic shape here is especially meant that, with the loads that occur when the space holder is in use, i.e. especially at the site of implantation, elastic deformation of the cylinder-like base body occurs in an order of magnitude appropriate to service use. By solid cylinder is meant that especially no lattice-like or framework hollow structure such as a cylinder pipe is intended. However, surface structures, such as grooves, recesses and the like are also comprised in an otherwise solid body. By cylinder or cylinder-like is hereby also meant a shape derived from a circular cross-section, like a polygon, and oval shape or a pea shape that copies the vertebrae.

The provision of a completely elastic-flexible solid cylinder facilitates limited movement of the body parts joined by the space holder towards each other as well as flexible alignment of the space holder with individual adjacent body parts. This markedly increases the comfort of the patient receiving this implant since, unlike a rigid space holder, a flexible, elastic space holder with good load distribution not only increases mobility but also, for example in the case of vibration, reduces loads on the adjacent body parts and thereby increases wearing comfort.

The use of a solid cylinder as the main component of a space holder that does not impair the means by which the space holder attaches to or grows into the flesh at the site of implantation is made possible by the fact that appropriate provision is made at the ends of the cylinder-like body for connection with adjacent body parts. Especially, it has proven advantageous to make provision for corresponding rings or cylinder pipe-shaped elements whose shape approximately resembles the lattice-like cylinder pipe-like elements that have so far been used as the base body. Especially, these means for connecting the space holder to adjacent body parts have protrusions, such as serrations or teeth extending in axial longitudinal direction, for penetration into adjacent body parts, especially bones, cartilage and the like, as well as recesses, apertures and/or cavities for enabling body tissue to grow into the recesses, apertures and/or cavities. In this way, adequate immobilisation of the space holder in the tissue of the implantation site is ensured.

Since, however, the means for connecting the space holders to adjacent body parts preferentially only take up a short section at the ends of the cylinder-shaped base body, it has proved advantageous to make corresponding adjustments to the shape of the cylinder pipe-like rings or pipes relative to the known shapes of the lattice-like, cylinder-pipe-shaped base bodies.

For example, it has proven advantageous to make provision for a wave-lice ring as the means for connecting the space holder to the adjacent body parts at the ends of the cylinder-like base body, said ring being notable for a wave-like arrangement of fillets or a zigzag arrangement of fillets around the body surface. In this way, serrations and cavities are formed simply on the upper and lower side of the ring, which are capable of being used for connecting to adjacent body parts or body tissue.

In a preferred embodiment, the cylinder pipe-like rings or pipes for connecting the space holder to adjacent body parts are provided with a series of diamond- or rhombus-like cavities around the cylinder pipe, with the rows of diamond-like cavities in the axial direction offset from each other by half a diamond. With this shape, the operator can simply adjust the length of the lattice-like or network-like pipes to the desired length. This may be done simply by cutting off the pipes at the desired length transverse to the longitudinal direction, as a result of which corresponding serrations are again formed at the cut end by the diamond-like cavities.

The lattice-like or network-like pipes or rings, which are used as means of connecting the space holder to adjacent body parts, may be connected in various ways to the cylinder-like base body, especially by non-positive or frictional, positive or material union means. For this purpose, provision can be made on the cylinder-like base body and/or the network-like, lattice-like or wave-like pipes or rings, i.e. the means of connection, for corresponding holding means for mutual engagement or holding. Especially, it has proved advantageous here to make provision on the pipe-shaped or ring-shaped connecting means for especially radially inward pointing prongs or serrations that engage with the cylinder-shaped base body or, for example, can be co-moulded during the manufacture of the cylinder-like body.

To obtain the elasticity or flexibility of the cylinder-like base body, a correspondingly elastic material may be used to form the cylinder-shaped body, in particular, bio-compatible polymer, such as high molecular polyethylene or medical grade silicone rubber. Apart from homogeneous formation of the cylinder-like body from a single material, it is also conceivable to realize the cylinder-like body, especially the solid cylinder, from composite material or as a multicomponent part, since, especially through appropriate selection of the corresponding components or of the composite material, particularly ideal adjustment to the desired properties is facilitated. However, it is important here that all components have corresponding elasticity in order that problems in the interaction of rigid and elastic components may be avoided.

Preferentially, the elastic material is also to be chosen such that the cylinder-shaped body, expressed in terms of its longitudinal direction, may be extended or compressed by approximately 0.5 to 20%, especially 1 to 15%, or/and the intended means of connecting the ends can swivel by approximately 0.5 to 10°, especially 1 to 6° out of the longitudinal axis of the space holder. A correspondingly adjusted space holder thus facilitates the requisite mobility of the space holder combined with adequate stability.

It has proved particularly advantageous for the cylinder-shaped body to be formed from a cylinder-like core and a cylinder-like sleeve arranged co-axially with the core, with the core and sleeve capable of having different mechanical properties. Preferentially, the core, which has to sustain less extension, is made more rigid, whereas the sleeve has greater elasticity to facilitate larger extension.

Figure 2:
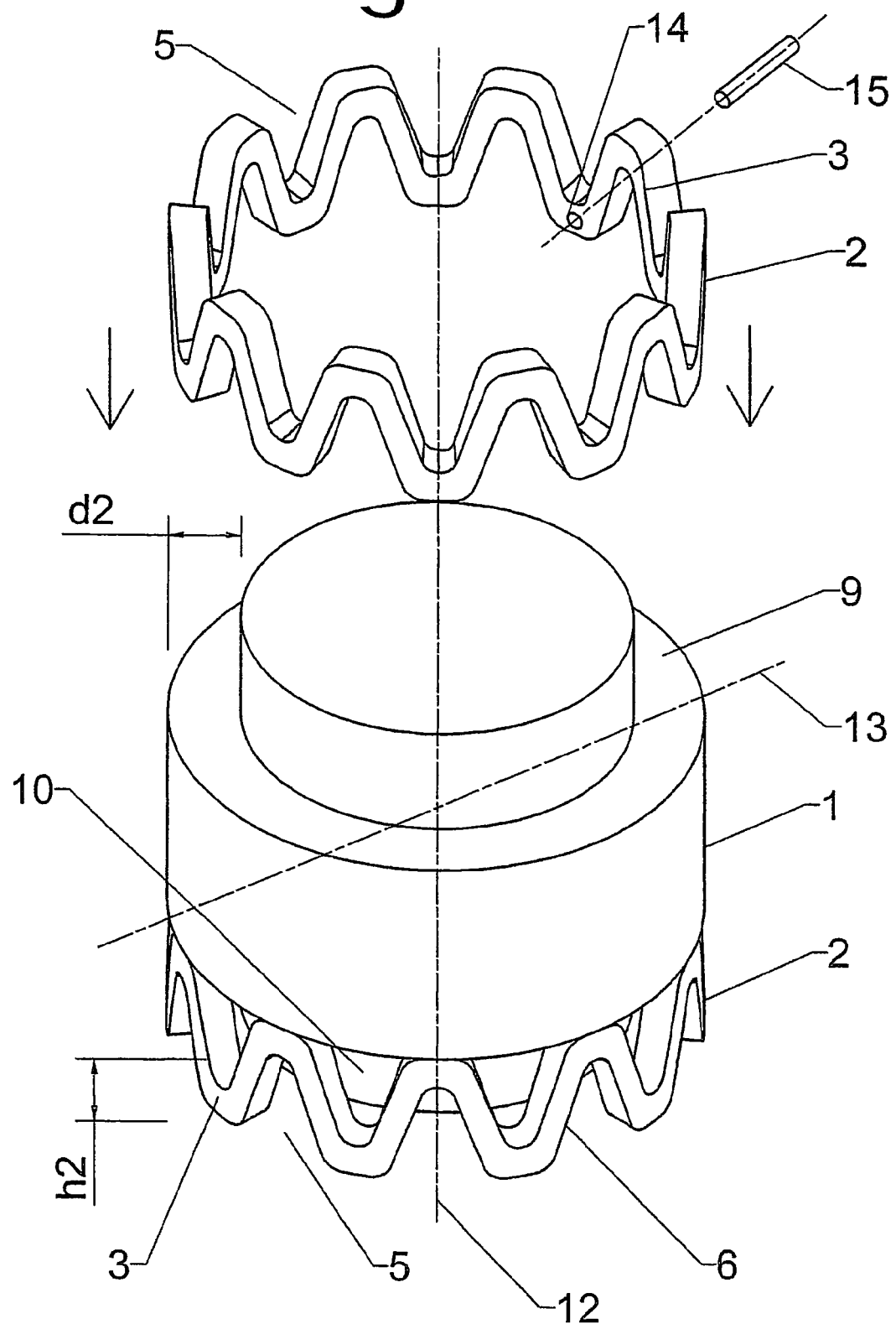
Figure 3:
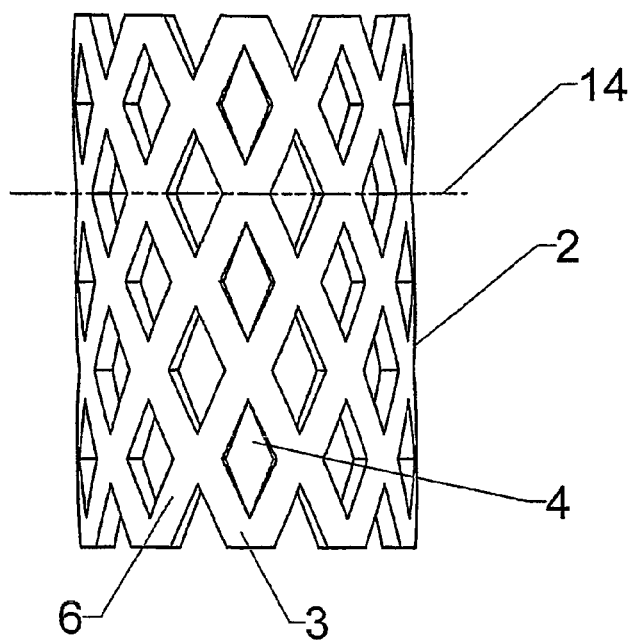
Figure 4:
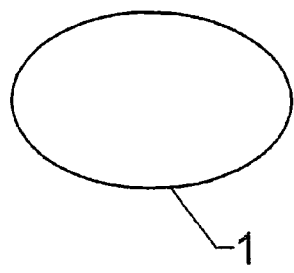

Further advantages, characteristics and features of the object of the present invention become clear from the following detailed description of two sample embodiments. The purely schematic diagrams show the following:

FIG. 1 a 3D view of a first space holder of the invention in a partially exploded view, and in FIG. 2 a 3D view of a second space holder of the invention in a partially exploded view;

FIG. 3 a side view of a connecting ring with several rows of diamond shaped cavities arranged such that they are offset from each other in the axial direction by a half diamond;

FIG. 4 an oval cross-sectional shape of a cylinder-like base body; and

Figure 5:
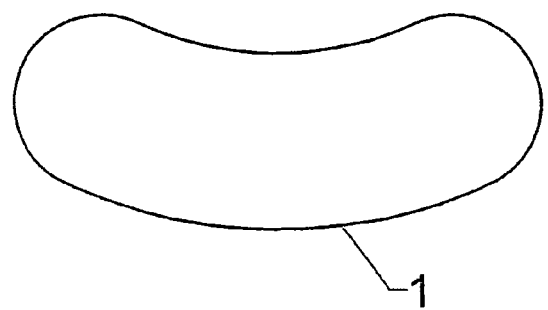

FIG. 5 a pea-shaped cross-sectional shape of a cylinder-like base body.

FIG. 1 shows a 3D view of a first embodiment of the space holder of the invention with a cylindrical body 1 having provision for two connecting rings 2 at the ends of the cylindrical body 1 for connecting the space holder to the adjacent body parts, e.g. bones or cartilage in, for example, the human body. Cylindrical body 1 is made as a solid cylinder from an elastic polymer, such as high molecular polyethylene or medical grade silicone, with cylinder-shaped body 1 being made up of two parts, namely a cylindrical core 8 and a cylinder pipe-shaped sleeve or cover 7, which is arranged coaxially around core 8. Due to the two-component structure of core 8 and sleeve 7, different materials having different properties, such as strength, elasticity etc, can be used for optimally adjusting the mechanical properties of cylinder-shaped body 1 to requirements.

Connecting rings 2, which are arranged at the ends of cylinder-shaped body 1, have identical shapes in the sample embodiment shown, but may also have different shapes. Connecting rings 2 possess an inner diameter that roughly corresponds to the outer diameter of cylinder-shaped body 1 such that they can be pushed over the ends of cylinder-shaped body 1. The outer diameter of cylinder-shaped body 1 can be made somewhat larger than the inner diameter of connecting ring 2 in order that tensioning of the cylinder-shaped body 1 and/or connecting ring 2 may cause the connecting ring to sit firmly by non-positive means on cylinder-shaped body 1. In this selected variant, connecting rings 2 project by a thickness $d_1$, which corresponds to the wall thickness of connecting ring 2, over the body surface of cylinder-shaped body 1. Furthermore, connecting rings 2 are arranged on cylindrical body 1 such that they project by a height $h_1$ in the axial direction beyond the ends of cylinder-shaped body 1. It is thus possible for serrations 3 provided for at the side ends of connecting rings 2 to engage with adjacent body tissue at the site of the implantation.

Connecting rings 2 in the embodiment shown in FIG. 1 are formed such that triangular cavities 5 at the two ends of connecting ring 2 create trapezoidal serrations 3, provision for which is made at the side opposite cylinder-shaped body 1 for engaging with and clinging onto adjacent body tissue.

In addition, connecting ring 2 has diamond-shaped cavities 4, provision for which is made such that they are adjacent to each other around the entire ring. As a result, connecting ring 2 is formed again to itself by a number of diamond-shaped interconnected fillets 6, with the tips of the diamonds formed by fillets 6 cut-off so that trapezoidal serrations 3 are formed. Since connecting ring 2 in the sample embodiment shown projects over cylindrical body 1 approximately from the centre of the diamonds 4, each diamond-shaped cavity 4 in the ring 2 shown in the lower part of FIG. 1 has an upper region 10 in which only a recess as far as the cylindrical body 1 is formed due to diamond-shaped cavity 4, whereas provision is made in lower region 11 for a fully open aperture (correspondingly in upper ring 2). Both recess 10 and aperture 11 enable the space holder to grow into and knit together with the body tissue.

Aside from the force fit or snug fit of the connecting rings on cylindrical body 1, there are other ways of effecting a permanent and especially non-twisting connection between connecting rings 2 and cylindrical body 1. For example it is possible to make provision for protrusions (not shown) on the inside of connecting rings 2 and to also mould, for example, the connecting rings 2 or the protrusions during the manufacture of cylinder-shaped body 1 by injection moulding into cylinder-shaped body 1, in which case the projections would then be enveloped and occluded by the plastic compound of cylinder-shaped body 1, as a way of effecting the permanent connection between cylinder-shaped body 1 and connecting rings 2. In addition, however, a large number of other connecting means and techniques are conceivable.

Through forming the cylinder-shaped body 1 as a solid body and especially as a two-component body with core 8 and sleeve 7, optimum load distribution and load accommodation are possible, with, especially by forming core 8 and sleeve 7 differently as regards mechanical properties, a desired property profile capable of being set. For example, core 8 can be designed to be more rigid than jacket 7 such that, given flexural stress on the space holder about the radial axis 13 shown by way of example, the especially highly extended or compressed external areas of sleeve 7 exhibit extensive yielding capability, whereas core 8, which only has to accommodate less extensive extension or compression, exhibits greater rigidity such that the space holder overall has the property of readily facilitating minor bending, while increasing bending is met with a disproportionate increase in resistance. But also axial extension or compression along longitudinal axis 12 is optimally effected by the elastic solid cylinder 1 of the embodiment shown in FIG. 1.

FIG. 2 shows a second embodiment of a space holder of the object of the invention in an illustration corresponding to FIG. 1. Therein, the same or similar components with identical references are shown so that, with the exception of the differences described below, the considerations above also apply here.

In the embodiment of FIG. 2, cylindrical body 1 is also made from an elastic polymer, with the exception that it is a single-piece body made from one component, i.e. cylinder-shaped body 1 is made from a single material in a single piece. However, the ends of cylinder-shaped body 1 have a reduced diameter for a limited length of the longitudinal axis 12 of cylinder-shaped body 1 such that a shoulder 9 is formed. The diameter is thereby reduced by twice the thickness $d_2$, which corresponds to the wall thickness of connecting ring 2, such that connecting ring 2 arranged at shoulder 9 is flush with the body surface of cylinder-shaped body 1.

In this embodiment, also, the connecting rings 2 are formed such that, in the arrangement in shoulder 9 of cylinder-shaped body 1, they project over the ends of cylinder-shaped body 1 by a height $h_2$ in order again to give the spikes 3 formed at the ends the possibility of engaging with adjacent body tissue at the site of implantation.

The embodiment shown in FIG. 2 also differs from the embodiment shown in FIG. 1 as regards the shape of connecting rings 2. The connecting rings 2 used here are notable for the fact that they have a wave-like or a zigzag shaped arrangement of fillets 6, such that triangular cavities 5 are formed between the fillets 6 at the ends and trapezoidal spikes 3 are again present between triangular cavities 5.

By virtue of the arrangement of connecting rings 2 in shoulders 9 of cylinder-shaped body 1, the triangular grooves 5 on the side facing cylinder-shaped body 1 form recesses 10 with cylinder-shaped body 1 that again enable the space holder to grow into the body tissue.

On the upper connecting ring 2 of FIG. 2 is shown by way of example the manner in which, for example, a connection may be effected between connecting rings 2 and cylinder-shaped body 1 by rods 15 projecting radially inward. In this regard and also by way of example is shown in connecting ring 2 aperture 14, through or into which rod 15 can be pushed or screwed such that it projects radially inward inside connecting ring 2. Rod 15 can be fixed to connecting ring 2 by suitable means of attachment, such as thread and counter-nut. Connecting rings 2 prepared in this way can, for example, then be inserted into an injection mould so that cylinder-shaped body 1 can then be moulded from a bio-compatible polymer. Radially inwardly projecting rods 15 of connecting rings 2 are then occluded in cylinder-shaped body 1 and produce a permanent, especially also a non-twisting connection between connecting rings 2 and cylinder-shaped body 1. Admittedly, it is also conceivable to produce cylinder-shaped body 1 beforehand, to push connecting rings 2 onto shoulders 9 and and then to press rods 15 through apertures 14 into cylinder-shaped body 1 or into the polymer material of cylinder-shaped body 1 or to guide them into corresponding holes and then to secure rod 15 in a suitable way, e.g. via screw connections on connecting ring 2. In addition to the connecting possibilities described explicitly here for connecting connecting rings 2 and cylinder-shaped body 1, numerous other suitable connecting techniques are conceivable.

FIG. 3 shows a side view of an alternative connecting ring 2 with several rows of diamond-shaped cavities that are offset to each other in the axial direction by a half diamond.

As indicated by the dashed line 14 in FIG. 3, a connecting ring 2 designed in this way can be shortened to the corresponding desired length by cutting along cutting line 14 of connecting ring 2 such that spikes 3 are again formed at the point of separation by diamond-shaped-connected fillets 6.

FIGS. 4 and 5 are schematic cross-sectional diagrams of the different cross-sectional shapes of cylinder-like body 1, with FIG. 4 showing an oval cross-sectional shape and FIG. 5 a pea-shaped cross-section.

The invention claimed is:

1. A space holder for vertebrae or intervertebral discs for implantation into living human or animal organisms, the space holder comprising:
   a cylinder-like body having a first end and a second end, the body defining a longitudinal axis extending from the first end to the second end and having an outwardly facing cylinder-like surface extending in a direction of the longitudinal axis at each of the first and second ends of the cylinder-like body;
   first and second connecting members to connect to adjacent body parts provided at the first and second ends, respectively, of the cylinder-like body, each of the first and second connecting members having a ring-like shape and having an inwardly facing ring-like surface extending primarily in a direction of the longitudinal axis that is connected to and contacts the outwardly facing cylinder-like surface at the first and second ends of the cylinder-like body, respectively;
   wherein each of the first and second connecting members has a central opening therethrough having an outer diameter defined by the inwardly facing ring-like surface such that at least a portion of the first end and at least a portion of the second end of the cylinder-like body is exposed through the central opening of the first and second connecting member, respectively;

wherein the cylinder-like body is formed as a solid body from at least one material that is elastically deformable under the intended conditions of use;

wherein the space holder is compressible and extensible in an axial direction and is bendable about a radial axis of rotation; and wherein the first and second connecting members have at least one cavity comprising a recess extending only as far as the cylinder-like body between the ends of the cylinder-like body and a fully-open aperture outside the ends of the cylinder-like body.

2. The space holder of claim 1, wherein the inwardly facing ring-like surface of each of the first and second connecting members defines inner surfaces of protrusions that project in a direction of the longitudinal axis of the cylinder-like body away from the cylinder-like body from the first end and the second end, respectively.

3. The space holder of claim 2, wherein each of the first and second connecting members have a ring-like wall perforated therethrough.

4. The space holder of claim 3, wherein the ring-like wall of the first and second connecting members includes a large number of fillets that are connected in one of a diamond shape and a wave shape.

5. The space holder of claim 2, wherein the protrusions of the first and second connecting members at least partially protrude past the ends of the cylinder-like body.

6. The space holder of claim 2, wherein the protrusions have at least one of a triangular and trapezoidal shape.

7. The space holder of claim 1, wherein the first and second connecting members are connected by at least one of non-positively, frictionally, by form fit, and union of the members to the cylinder-like body.

8. The space holder of claim 1, wherein the cylinder-like body, expressed in terms of its longitudinal direction, is at least one of elastically extendible and compressible by 0.5 to 20%.

9. The space holder of claim 8, wherein the cylinder-like body is at least one of elastically extendible and compressible by 1 to 15%.

10. The space holder of claim 1, wherein the cylinder-like body is bendable elastically about a radial axis, such that the first and second connecting members are swivelable by approximately 0.5 to 10° out of a longitudinal axis of the space holder.

11. The space holder of claim 10, wherein the cylinder-like body is bendable elastically about a radial axis such that the first and second connecting members are swivelable by 1 to 6° out of the longitudinal axis of the space holder.

12. The space holder of claim 1, wherein the cylinder-like body is formed from elastic material, which comprises a biocompatible polymer.

13. The space holder of claim 12, wherein the cylinder-like body is formed from at least one of high molecular polyethylene and medical grade silicone rubber.

14. The space holder of claim 1, wherein the cylinder-like body is at least one of composite material and a multi-component part.

15. The space holder of claim 1, wherein, the solid body comprises a cylinder-like core and a co-axial cylinder pipe-like sleeve.

16. The space holder of claim 15, wherein the sleeve and the core are different materials having different elasticity.

17. The space holder of claim 1, further comprising a holding member to connect the cylinder-like body and the first and second connecting members together.

18. The space holder of claim 17, wherein the holding member comprises a radially inwardly protruding rod on at least one of the first and second connecting members.

19. The space holder of claim 18, wherein the holding member comprises an anti-twist stop.

20. The space holder of claim 1, wherein the first and second connecting members are molded into or onto the cylinder-like body.

21. The space holder of claim 1, wherein the cylinder-like body has a shoulder on each of its ends for receiving the first and second connecting members such that the cylinder-like body and the first and second connecting members are flush along an outwardly facing cylinder-like surface of the space holder.

* * * * *

UNITED STATES PATENT AND TRADEMARK OFFICE
CERTIFICATE OF CORRECTION

| | | |
|---|---|---|
| PATENT NO. | : 7,896,918 B2 | |
| APPLICATION NO. | : 10/568262 | |
| DATED | : March 1, 2011 | |
| INVENTOR(S) | : Jurgen Harms et al. | |

It is certified that error appears in the above-identified patent and that said Letters Patent is hereby corrected as shown below:

In the Specifications

Column 3, line 5         Delete "wave-lice" Insert -- wave-like --

Column 5, line 24        After "profile" Insert -- is --

Signed and Sealed this
Seventh Day of February, 2012

David J. Kappos
*Director of the United States Patent and Trademark Office*